United States Patent [19]
Tinder

[11] 3,931,677
[45] Jan. 13, 1976

[54] DIE STONE CASTING FOR DENTAL RESTORATION

[76] Inventor: Lawrence E. Tinder, 2900 Sawmill Gulch Road, Pebble Beach, Calif. 93953

[22] Filed: Feb. 6, 1974

[21] Appl. No.: 440,208

Related U.S. Application Data

[63] Continuation-in-part of Ser. No. 340,937, March 13, 1973, Pat. No. 3,832,777.

[52] U.S. Cl. .................................................. 32/11
[51] Int. Cl.². ........................................ A61C 13/00
[58] Field of Search .......... 24/137, 138, 257; 32/11, 32/40 R

[56] References Cited
UNITED STATES PATENTS

| | | | |
|---|---|---|---|
| 2,851,728 | 9/1958 | Spalten et al. | 32/11 UX |
| 3,100,324 | 8/1963 | Tutino et al. | 24/137 R |
| 3,418,698 | 12/1968 | Holcomb | 24/137 A |
| 3,552,018 | 1/1971 | Zahn | 32/11 |

*Primary Examiner*—Robert Peshock
*Attorney, Agent, or Firm*—Lynn G. Foster

[57] ABSTRACT

An assembly for creating die stone castings for dental restoration (inlays, crowns, and fixed bridges) comprising (a) a die pin setter comprising a flexible plastic tube or rod positionable in substantially superimposed relation above the curvilinear array of cavities in a dental impression formed of elastic material, (b) a die pin holder comprising a series of bifurcated clips each forced down over the plastic tube in press-fit relation but nonetheless accommodating rotation of each clip in respect to the plastic tube into generally coaxial relation with an adjacent impression cavity, and (c) a dual dowel or die pin unit associated with each clip with at least one upper pin of the unit press-fit in depending relation into a blind bore of the associated clip locating two lower dowel or die pins in the adjacent impression cavity. The depending association between each clip and its dual pin unit allows relative rotation to aid in properly orienting the two lower die pins in the adjacent impression cavity. Also, by using two upper die pins in lieu of one, either may be press-fit into the blind bore of the adjacent clip, again insuring accurate, simple and quick placement of the die pins in the impression cavity.

8 Claims, 2 Drawing Figures

DIE STONE CASTING FOR DENTAL RESTORATION

BACKGROUND

CONTINUITY

This application is a continuation-in-part of my earlier and presently copending U.S. Pat. application Ser. No. 340,937, filed Mar. 13, 1973 and now U.S. Pat. No. 3,832,777 issued Sept. 3, 1974.

FIELD OF THE INVENTION

The present invention relates generally to die stone casting for dental restoration and more particularly to methods and apparatus, preferably comprising a die pin setter in the nature of a flexible plastic tube, a series of die pin holders in the nature of bifurcated clips and a dual dowel pin unit associated with each clip for die stone casting whereby inlays, crowns and fixed bridges are fabricated.

PRIOR ART

Heretofore, die stone casting in the course of dental restoration utilized very expensive precision equipment not easily adaptable for use from one impression to the next impression, occupied extensive periods of time, frequently resulted in intolerable accuracies in the work product, and required technically trained personnel. While from U.S. Pat. No. 3,704,519 it is known to use two pins in dental restoration work, the apparatus and methods of the present invention are otherwise totally dissimilar.

BRIEF SUMMARY AND OBJECTS OF THE INVENTION

The present invention overcomes or at least substantially alleviates the above-mentioned limitations of the prior art by providing novel methods and apparatus, which apparatus is relatively inexpensive, requires only limited time to use and results in an accurate work product, even when operated by non-technical persons. The preferred apparatus comprises a die pin setter in the nature of a flexible plastic tube or rod the arcuate or curvilinear configuration of which configuration may be almost instantaneously altered from impression to impression to be substantially superimposed over the array of cavities in any given impression. Bifurcated clips, serving as die pin holders, are forced down over the plastic tube or rod in press-fit relation but nonetheless accommodate rotation of each clip into generally coaxial relation with the adjacent impression cavity and are also individually readily removable by simply manually lifting the clip from its press-fit disposition over the flexible tube or rod. Dual dowel or die pin units are used, one with each clip, in depending press-fit relation thereto so that at least two lower dowel or die pins extend well into the adjacent impression cavity. Thus, when the lower two die pins are positioned in the die stone material placed in the impression cavity and the material has set, relative rotation between each die stone segment (following cutting) and the associated die pin unit is prohibited. Naturally, the press-fit relation between each clip and dual die pin unit allows rotation of the pin unit in respect to the clip to aid in prompt and accurate orientation of the two depending dowel pins in each impression cavity. Moreover, if two upper press-fit accommodating pins are provided, either may be associated with the adjacent clip, again for speedy, accurate and inexpensive pin orientation.

Accordingly, it is a primary object of the present invention to provide novel methods for dental restoration.

Another paramount object of the present invention is to provide improved apparatus for dental restoration.

A further and no less important object of the present invention is to provide dental restoration equipment comprising a die pin setter in the nature of a flexible plastic tube or rod the curvilinear configuration of which may be readily repositioned from impression to impression without exchange of equipment, expensive and time consuming procedures and without the need for technical personnel.

A further dominant object of the present invention is the provision of dental restoration apparatus comprising bifurcated clips serving as die pin holders which are pressed down over a die pin setter of curvilinear configuration accommodating immediate placement and removal and ready pin orientation in an adjacent impression cavity.

An additional principal object of this invention is the provision of dental restoration apparatus comprising dual die pin units which are each press-fit in depending relation to an associated die pin holder so as to be rotatable whereby two lower die pins are accurately and immediately positioned in an adjacent impression cavity and ultimately non-rotatably retained within the die stone once cast and set.

An additional significant object of the present invention is the provision in a dental restoration apparatus of dual die pin units each adapted to be press-fit in depending relation to a die pin holder in either of two upper pins to accommodate initial relative rotation in respect to the holder whereby two lower pins are accurately and instantaneously positioned in an impression cavity.

These and other objects and features of the present invention will be apparent from the following detailed description, taken with reference to the accompanying drawings.

DETAILED DESCRIPTION OF THE ILLUSTRATED APPARATUS

Reference is made now specifically to the drawings, which illustrate a presently preferred dental restoration assembly, generally designated 10. While it is to be appreciated that the assembly 10 will be associated with holding or support equipment, such is not essential to an implementation or a complete description of the present invention. It is preferred that the assembly 10 be fundamentally supported or carried by a jig which includes a base, a dental impression tray clamp and a jig mount such as is described and claimed in my copending U.S. Pat. application Ser. No. 340,937, filed Mar. 13, 1973, to which reference may be made for a more thorough understanding of the present application which is a continuation-in-part thereof.

Figure 1:
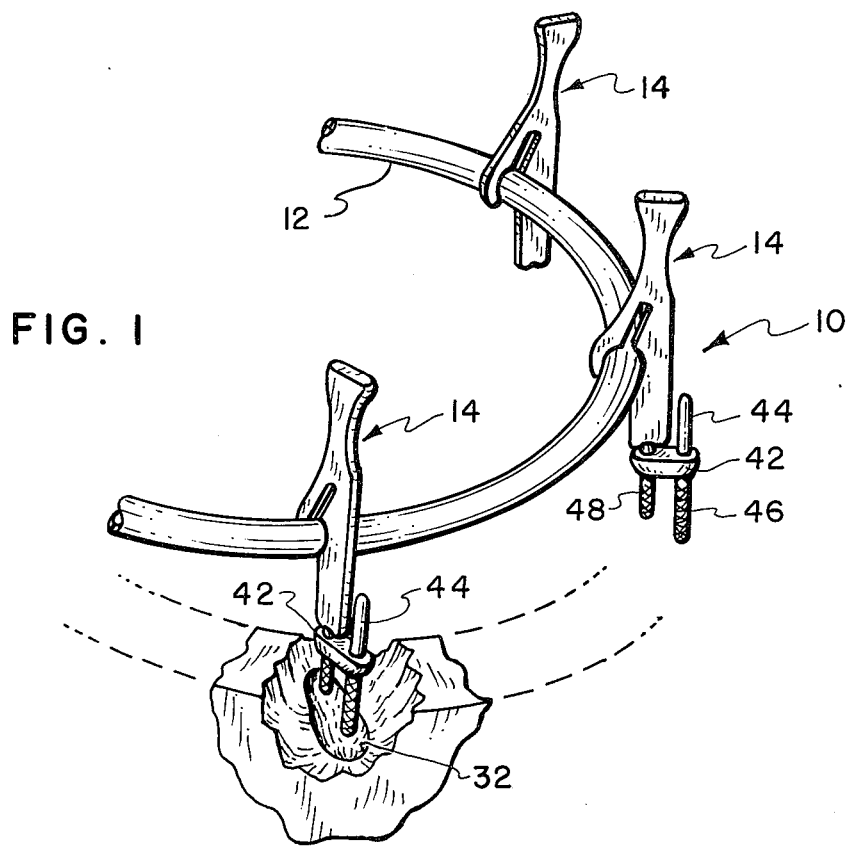
FIG. 1 is a fragmentary prospective representation of a presently preferred dental restoration assembly comprising a flexible plastic tube functioning as the die pin setter member, a series of one-piece plastic clips press-fit from above over the flexible plastic tube and a dual die pin unit depending from each clip.

The assembly 10 comprises a die pin setter member in the nature of a flexible plastic tube or rod 12. One suitable type of plastic tube is saliva ejector stock, the plastic of which is readily yieldable as is a metal reinforcing element imbedded within the plastic. By utilizing the jig mount of U.S. Pat. application Ser. No. 340,937, the curvilinear configuration of the die pin setter tube 12 may be altered from dental impression to dental impression so as to be essentially superimposed thereover. This may be accomplished almost immediately without technical expertise. It is to be appreciated that flexible tube 12 may be positioned in a horizontal plane as illustrated in FIG. 1 or in an erected condition so as to be essentially out of the way when necessary or desirable.

Assembly 10 also comprises an array of die pin holders in the nature of bifurcated clips 14 preferably formed of rigid plastic material, such as nylon, in one piece through injection molding, notwithstanding the fact that other materials and methods of fabrication could be relied upon. Each clip 14 is press-fit downward over the curvilinear flexible plastic tube when disposed in the horizontal plane so as to constrict the diameter of the tube 12 forcing the memory of the material from which tube 12 is made to exert an outward force upon the clip 14 thereby tending to retain each clip 14 in a stationary condition force-fit or press-fit mounted upon the tube 14.

Each clip 14 comprises an upwardly extending contoured handle 16, a central bifurcated section 18, a downwardly extending side finger 20 and a downwardly extending axial finger 22. Fingers 20 and 22 are separated by an elongated narrow slot 24. The slot 24 opens into a generally circular region, a semi-circle 26 thereof being formed on the inside of the side finger 20 and a semi-circle 28 thereof being formed on the inside of the axial finger 22. Together the two essentially semi-circular notches 26 and 28 form an essentially circular confinement the diameter of which is slightly less than the diameter of the tube 12.

The lower portion of the finger 22 comprises an axial downwardly opening blind bore 30, having a length and diameter for receiving a pin as hereinafter more fully described. In short, each clip 14 is readily press-fit over the tube 12, after or before it is configured to be superimposed rather exactly over the arc of cavities in a dental impression placed under the tube 12. Each clip 14 is force-fit at semi-circular grooves 26 and 28 over the tube 12, causing the slot 24 to initially spread somewhat, so that the memory of the tube 12 holds the clip in whatever orientation is manually set. Clearly, the orientation may be readily altered by gripping the handle 16 between the fingers and rotating the clip 14 about the tube 12, preferably causing the axial finger 22 to become essentially aligned with the axis of an impression cavity 32 (FIG. 1). This requires negligible time, is extremely accurate and does not necessitate use of highly trained personnel.

Figure 2:
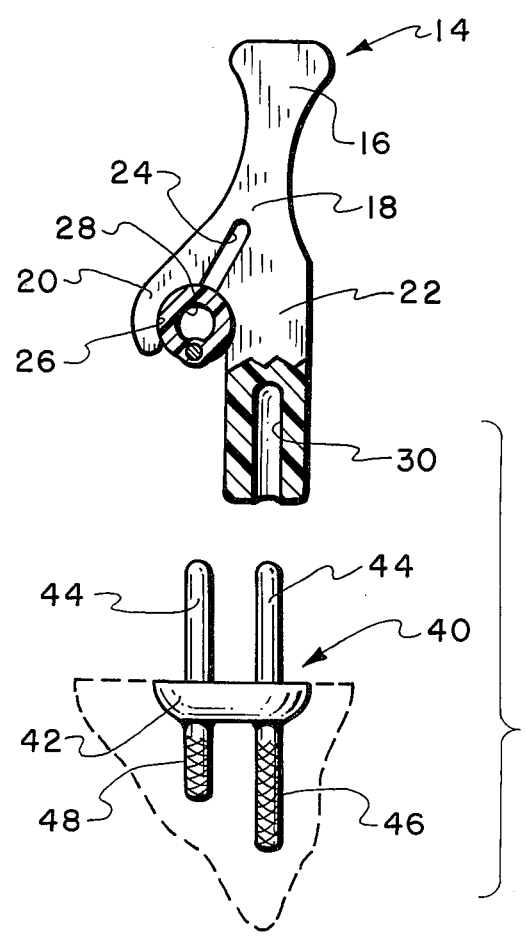
FIG. 2 is an exploded front elevation view of one clip, (force-fit down upon the flexible plastic tube) and a dual pin unit.

The assembly 10 also comprises a dual die pin unit 40, but it is to be appreciated that a single die pin placed in blind bore 30 and extending axially into the adjacent impression cavity 32 could also be used in conjunction with the clip 14 and a suitable die pin setter member. The dual die pin unit 40, however, comprises a central bumper or abutment 42, downwardly tapered about its periphery and integrally joined (preferably by one-piece injection molding techniques using nylon or another suitable plastic) to two upwardly projecting clip engagable pins 44. Either pin 44 may be press-fit into the blind bore 30, depending upon which will more accurately place the depending portion of the dual pin unit 40 most appropriately within the adjacent impression cavity 32. It is to be appreciated that the length and diameter of each of the two upper clip engagable pins 44 is of such a nature as to accommodate force fitting of either pin 44 within and removal from the blind bore 30 of the adjacent clip 14. Two depending pins of dissimilar lengths 46 and 48, to match the configuration to the impression cavity 32, are integral with the central bumper 42. Each pin 46 and 48 is adapted to be placed within the impression cavity 32 as shown in FIGS. 1 and 2 so that when the impression cavity 32 is filled with die stone material, and the pins 46 and 48 are imbedded therein, the dual pin unit 40 is non-rotatably retained by the die stone casting after it has set and tooth sections cut therefrom. It is preferred that the exterior surface of the pins 46 and 48 be knurled or otherwise roughened to accommodate satisfactory bonding between the die stone material and the pins.

After the die stone material has been placed in the array of impression cavities, each containing imbedded pins 46 and 48 depending from the dual pin unit 40 therein and a die stone casting obtained therefrom, conventional techniques are used to mount the die stone casting upon a base material into which pins 44 extend and to cut the die stone casting into separate tooth segments. The base material releasably holds the tooth segments during "waxing-up" and completion of the inlay or the like using conventional techniques. During these procedures, it is significant to have pins 44 available for accurately returning the associated die stone tooth segment to its proper position in the base material which preserves the array of the initial impression and that the pins 46 and 48 be retained imbedded within the die stone material whereby rotation between the pin unit and the tooth segment is pre-empted. It is also to be appreciated that, once the die stone material has been placed in the array of impression cavities and set with pins 46 and 48 imbedded therein, the tube 12 and each clip 14 may be immediately removed, with the investment of negligible time.

Restated, the present assembly 10 comprises apparatus and provides methodology which produces highly accurate die stone casting for dental restoration with a minimum of time invested, without expensive equipment and procedures and can utilize the services of non-technical personnel to produce the castings of high precision.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A die pin holder comprising an elongated clip having a major axis and three ends, the clip comprising:
   means at one end of the clip along said axis for releasably receiving in depending generally axial relation at least one die pin;

a body disposed central of the three ends comprising a bifurcated section defining an inverted Y, the apex region of which defines a downwardly directed opening adapted to be force fit over die pin setter means;

a free normally upwardly directed second end along said axis comprising a handle for manually gripping the clip to cause the clip to be placed downwardly in and removed upwardly from said force fit relation with the die pin setter means;

said third end projecting at an acute angle in respect to said axis, with said downwardly directed opening at said apex region being sized to initially slightly under match the cross sectional size of the die pin setter means over which the die pin holder is force fit to enlarge the size of said opening equal to the size of the die pin setter means.

2. A die pin holder according to claim 1 further comprising a slot at said apex region extending angularly into the central body to accommodate facile spreading of the holder of the bifurcated section during placement downwardly upon and removal upwardly from the die pin setter means.

3. A die pin holder according to claim 1 wherein said one end means comprises an axial blind bore adapted to receive the at least one die pin in force-fit releasable relation.

4. A one-piece die pin unit comprising:

a central enlarged body;

at least one pin integral with and extending essentially perpendicular upwardly away from the body, said at least one pin adapted to be force fit into releasable depending engagement with a receptacle of a die pin holder;

at least two pins integral with and extending downwardly in spaced essentially parallel relation essentially perpendicular away from the body in a direction essentially opposed to the at least one upwardly directed pin, said at least two downwarly directed pins adapted to be placed in depending relation within die stone material within a dental impression cavity prior to the initial set of the material.

5. A dental restoration assembly comprising:

a one piece elongated flexible plastic tubular die pin setting member disposed in an adjustable curvilinear configuration;

at least one die pin holding plastic clip having an upwardly projecting manual handle, a central bifurcated section, from which two downwardly extending fingers depend, the bifurcated section being force fit downwardly over the tubular member allowing manual radial rotation of the clip upon the axis of the tubular member, one of said fingers being longer than the other, the longer finger having a blind bore in the lower end thereof;

a dual die pin unit comprising an upwardly extending pin force fit into said blind bore, a central body portion and at least two downwardly extending pins adapted to be placed in die stone material within a dental impression cavity before the material has set.

6. A method of supporting an array of die pin holders upon a die pin setting member, comprising the steps of:

shaping a one piece yieldable plastic tubular die pin setting member into a curvilinear essentially superimposed relation over a dental impression;

force fitting one bifurcated die pin holder downwardly over the tubular member above each impression cavity in releasable relatively radially rotatable fashion with a portion of the bifurcated holder projecting downwardly toward the associated cavity;

force connecting at least one die pin unit to said downwardly projecting portion of the die pin holder in depending releasable relatively rotatable fashion; and imbedding only a lower part of the die pin in die stone placed within the cavity.

7. A method as defined in claim 6 wherein said force connecting step comprises placing one rod portion of the die pin unit in depending force fit relation in a blind bore of the projecting portion of the die pin holder and causing at least two other spacing rod portions to extend downwardly into the die stone receiving cavity.

8. In a dental restoration and die pin assembly, the improvement comprising die pin setter means comprising a length of small diameter elongated deformable plastic material with memory having two ends and placed in a curvilinear horseshoe configuration, each end of the elongated plastic material being secured to spaced selectively settable jig mount site means, whereby each change in the location of each jig mount site means alters the curve defined by the plastic material.

* * * * *